(12) United States Patent
Mavridis et al.

(10) Patent No.: US 7,834,174 B2
(45) Date of Patent: Nov. 16, 2010

(54) PER-6-GUANIDINO-, ALKYLAMINO-CYCLODEXTRINS, METHODS OF THEIR SYNTHESIS AND THEIR USE FOR THE COMPACTION OF DNA AND INTERCELLULAR DELIVERY

(76) Inventors: Irene M. Mavridis, 15 Panagiotou str, Panagou, 156 69 Athens (GR); Konstantina Yannakopoulou, 49 28th Octovriou str, Vrjlissia 15235, 15235 Athens (GR); Kyriaki Eliadou, 10 Costi Palama str, Kaisariani, 16122 Athens (GR); Nikolaos Mourtzis, 21 Nikomideas str, Peristeri, 12134 Athens (GR); Chrysi Aggelidou, 18 Vera str & Andromachis, Palaio Faliro, 17564 Athens (GR)

( * ) Notice: Subject to any disclaimer, the term of this patent is extended or adjusted under 35 U.S.C. 154(b) by 604 days.

(21) Appl. No.: 11/662,450

(22) PCT Filed: Apr. 21, 2005

(86) PCT No.: PCT/GR2005/000013
§ 371 (c)(1),
(2), (4) Date: Mar. 9, 2007

(87) PCT Pub. No.: WO2006/027631
PCT Pub. Date: Mar. 16, 2006

(65) Prior Publication Data
US 2008/0119431 A1 May 22, 2008

(30) Foreign Application Priority Data
Sep. 10, 2004 (GR) .......................... 20040100361

(51) Int. Cl.
*A61K 31/713* (2006.01)
*A61K 31/724* (2006.01)
*C12N 15/63* (2006.01)

(52) U.S. Cl. ....................... 536/103; 536/46; 514/44 R; 514/58; 435/455

(58) Field of Classification Search ....................... None
See application file for complete search history.

(56) References Cited

PUBLICATIONS

Prudden, A. et al "An outer-sphere ligand for uranyl carbonate" Chem. Comm. (2004) pp. 172-173.*
Khan, A.R et al., "Methods for Selective Modifications of Cyclodextrins", Chemical Reviews, American Chemical Society, vol. 98, No. 5, Jul. 1998, pp. 1977-1996.
Nozaki, T. et al., "Cycxlodextrins Modified With Polymer Chains Which Are Responsive to External Stimuli" Macromolecules, vol. 28, 1995, pp. 522-524.
Cryan, S.A et al., Cell Transfection With Polycationic Cyclodextrin Vectors, European Journal of Pharmaceutical Sciences, Elsevier, vol. 21, 2004, pp. 625-633.
Vizitiu et al., "Synthesis of Mono-Facially Functionalized Cyclodextrins Bearing Amino Pendent Groups", Journal of Organic Chemistry, ACS, vol. 62, No. 25, 1997, pp. 8760-8766.
Cotner, E.S et al., "Phosphotyrosine Binding by Ammonium and Guanidinium-Modified Cyclodextrins", J. Org. Chem., vol. 63, 1998, pp. 1737-1739.
Popielarski, S.R., "Structural Effect of Carbohydrate-Containing Polycations on Gene Delivery.3.Cyclodextrin . . . ", Bioconjugate Chem., vol. 14, Mar. 22, 2003, pp. 672-678.
Ashton, P.R et al., "Amino Acid Derivatives of Beta-Cyclodextrin", Journ. of Org. Chem., ACS, vol. 61, No. 3, Feb. 9, 1996, pp. 903-908.
Nozaki, T et al., Photo-Responsive Catalysis by Thymine-Cyclodextrin Conjugates, J. Chem. Soc., Perkin Trans 2, 1997, pp. 1217-1220.

* cited by examiner

*Primary Examiner*—Leigh C Maier
(74) *Attorney, Agent, or Firm*—Porzio, Bromberg & Newman, P.C.

(57) ABSTRACT

The invention relates to new compounds of type hexakis(6-deoxy-6-NH$(CH_2)_n$—$R^1$)α-cyclodextrin and heptakis(6-deoxy-6-NH$(CH_2)_n$—$R^1$)-(β-cyclodextrin, and octakis(6-deoxy-6-NH$(CH_2)_n$—$R^1$)-γ-cyclodextrin, where n=2-6 when $R^1$=$NH_2$ and n=0 when $R^1$=C(=NH)$NH_2$ and n=2-6 when $R^1$=NH—C(=NH)$NH_2$ and their use in the compaction of DNA and in cell permeation. The invention also relates to methods of synthesis of the above compounds.

8 Claims, No Drawings

PER-6-GUANIDINO-, ALKYLAMINO-CYCLODEXTRINS, METHODS OF THEIR SYNTHESIS AND THEIR USE FOR THE COMPACTION OF DNA AND INTERCELLULAR DELIVERY

The invention relates to new products hexakis-, heptakis- and octakis(6-deoxy-6-aminoalkylamino)- and -(6-deoxy-6-guanidino)- and -(6-deoxy-6-guanidinoalkylamino)cyclodextrins and their use in DNA compaction and in cell permeation. The invention also relates to methods for the synthesis of the above compounds.

Cyclodextrins (CDs) are cyclic oligosaccharides formed by α-D-glucose units (as in representation I) connected via 1,4-bonds. The most common consist of 6, 7 and 8 glucose units, respectively and are named α-, β- and γ-cyclodextrins. These oligomeric sugar molecules form a cavity as shown in the representation II and they are generally represented as truncated cones (representation III).

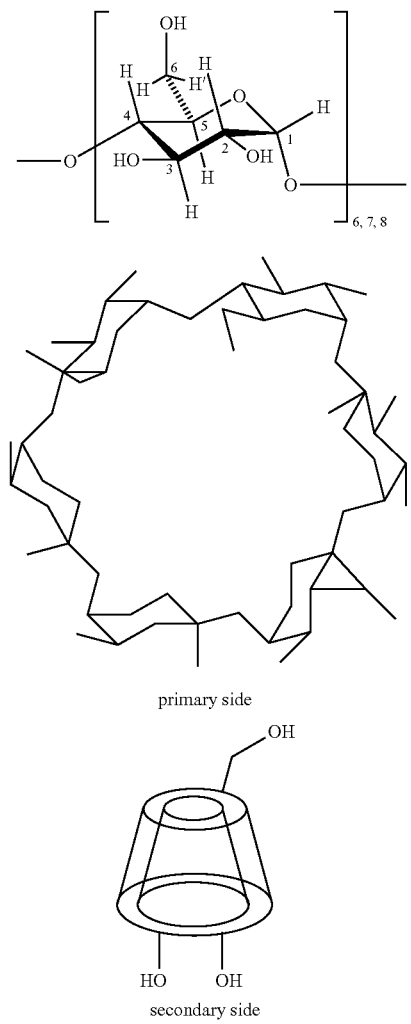

Cyclodextrins are structurally characterized by hydrophilic surfaces in the exterior, i.e. the primary hydroxyl groups (—CH$_2$OH) in the narrower rim of the cone and the secondary (—CHOH) in the wider rim, as well as by a lipophilic interior cavity at their center. Due to this last characteristic, they can enclose in their cavity organic molecules insoluble in water and thus form inclusion complexes. In the following paragraphs some basic terms used throughout the text are defined:

Synthetically modified cyclodextrins or cyclodextrin derivatives—refer to cyclodextrin compounds, in which the hydroxyl groups in carbon atoms C6 (of the primary side) or/and C2 or/and C3 (of the secondary side) have been substituted by one or more atoms or groups of atoms.

Per-substituted cyclodextrins—refer to synthetically modified cyclodextrins, in which all glucose units (six or seven or eight for α-, β-ή γ-cyclodextrin, respectively) bear the same substituent, that is in all carbon atoms C6 or/and all C2 or/and all C3, as specified. In the case that the substituent is not bound to the CD carbons through an oxygen atom the prefix "deoxy" is added.

Inclusion complexes of cyclodextrins—refer to the inclusion of one or more molecules or part of a molecule (guest molecule) inside the cavity of a natural cyclodextrin or a cyclodextrin derivative (host). The host and guest molecules interact through van der Waals forces, hydrogen bonds, hydrophobic interactions or polar interactions, which all stabilize the complex.

Cyclodextrins are generally water-soluble molecules and so are most of their inclusion complexes. This is an important property because molecules insoluble in water (pharmaceuticals, pheromones etc.) can form inclusion complexes with cyclodextrins and thus be solubilised in water. Therefore, cyclodextrins can increase the solubility and bioavailability of lipophilic drugs and some of them have been approved as molecular hosts of substances for pharmaceutical formulations. A number of such formulations are commercial [1].

β-Cyclodextrin is the commonest among the natural cyclodextrins and hundreds of its inclusion complexes (due to the proper dimensions of its cavity) with bioactive compounds have been studied. However, the solubility of β-cyclodextrin in water is limited (~16 mM in 25°). Therefore, the synthesis of derivatives with increased solubility in water has been desirable and such derivatives already exist commercially (2-hydroxypropyl-CD and methyl-CD). Moreover, additional derivatives are available commercially by specialized companies at very high prices.

During the last 15 years there is intensive research in the field of gene transfer into cells with the goal of defying diseases of genetic origin through intervention in the DNA of humans and animals (gene therapy). One of the basic limiting factors in the development of gene therapy is the absence of specificity and efficient targeting of the DNA transfer in the cell nucleus. There are two categories of vectors which can carry the gene to be transferred. The first constitutes various kinds of viral vectors and it is based in the known ability of viruses to invade host cells. However, there are problems in the use of viruses for gene transfer such as immunogenicity, the short duration of gene expression, the limited ability of the viruses to transfer foreign genes etc. [2]. Therefore, intensive research activity has been focused for some years now to a second group of non-viral vectors for transfer of DNA: organic compounds, mainly polyamine (polycationic) polymers [3]. This group also includes dendrimers and high molecular weight assemblies such as liposomes.

During the last five years the basic and necessary characteristics for the effective DNA transfer via non-viral vectors have been defined: biocompatibility, specific targeting, low toxicity, ability for DNA compaction, endocytosis, release from the endosome and DNA decompression to recover its functional structure. The cyclodextrin family of compounds satisfies the basic requirements for biocompatibility and low toxicity.

The synthesis of modified cyclodextrins has been improved in various aspects during the last 15 years. The mono-substitution at position 6 of the primary side is the most common process, being well characterized and reproducible. On the other hand, the substitution of all hydroxy groups of the primary side, i.e. 6, 7 or 8 for α-, β- and γ-cyclodextrin, respectively, is not an easy task for all types of substituents. Literature cites some examples of methods leading to well-characterized persubstituted cyclodextrins in the primary side [4]. However, the majority of persubstituted cyclodextrins, even these that are commercially available and they are used in pharmaceuticals, consists of mixtures of partially substituted isomers. Moreover, it is very common that the derivatives are not adequately characterized, because of the well-known property of cyclodextrins to form inclusion complexes with the reactants, a fact that makes the successful purification and complete characterization of the corresponding derivatives very demanding. Therefore, it is desirable to find simple methodologies expandable in the scale of many grams for the synthesis of pure, per-substituted cyclodextrins.

The synthesis of per(6-deoxy-6-amino)-α-, -β-και-γ-cyclodextrins is known [4], as well as the synthesis of mono- and bis-(6-deoxy-β-guanidino)-β-cyclodextrin, Both the above are purified after extensive use of chromatographic columns [5]. Per-amino derivatives of higher homology or per-guanidino derivatives, whose use for the compaction of DNA would be of interest, are not mentioned in the literature. Moreover, there is no report on per-6-substituted derivatives with aminoalkylamino- or guanidine-groups, or on any general methodology for the synthesis of the above to a degree of substitution greater than 95%.

During the last three years carbohydrate polymers consisting of cyclodextrins connected through chains of alkylguanidines have been developed, which were proven to be of low toxicity and capable of very effective gene transfer [6]. Moreover very recently, there appeared in the literature cyclodextrin derivatives bearing tertiary nitrogen atoms, which were used for the transfer of DNA in vitro [7]. However, these latter compounds presented the disadvantage that high excess of them was necessary for the compaction of DNA [7]. It should be noted that the amount of the organic compound needed for effective compaction is defined as the ratio is the reduced charge of the organic molecule to that of DNA. The reduced charge is defined as the ratio mass:charge for each molecule, which is 330 for the double stranded DNA.

The invention relates to the new class of compounds per (6-deoxy-6-aminoalkylamino)- and per(6-deoxy-6-guanidino)- and per(6-deoxy-6-guanidinoalkylamino)-derivatives of α-, β- and γ-cyclodextrins, where alkyl=—$(CH_2)_n$—, n=2-6. These are characterised by high solubility in water at neutral pH and display new bioactive properties. The new derivatives have been characterized completely as to their molecular structure with NMR spectroscopy using one dimensional (proton, carbon-13 and nitrogen-15 spectra) and two-dimensional experiments. Their purity is also confirmed by elemental analysis.

The invention also relates to the new molecules apen, bpen, gpen, in which six, seven or eight aminoethylamino-groups (derivatives of ethylenediamine) have replaced the primary hydroxyls of α-, β- and γ-cyclodextrin, respectively, and they are obtained starting from the natural cyclodextrins, converting them to per(6-deoxy-6-bromo)-derivatives, according to a method known in the literature, and subsequently subjecting the latter to the method described below as the "first method" using ethylenediamine.

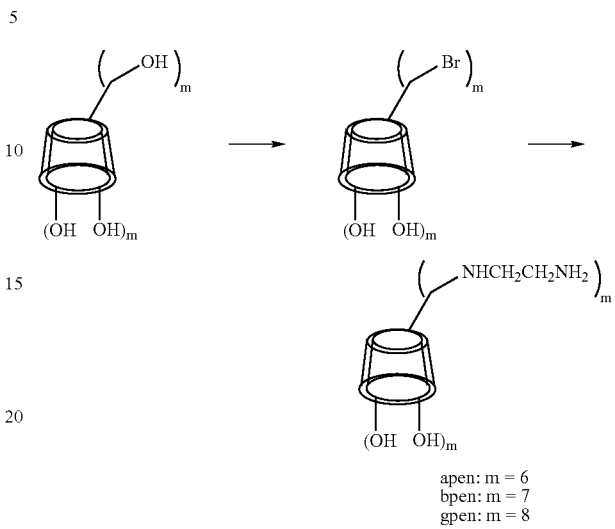

apen: m = 6
bpen: m = 7
gpen: m = 8

The invention also relates to the new molecules apren, bpren and gpren, in which six, seven or eight aminopropylamino-groups (derivatives of propylenediamine) have replaced the primary hydroxyls of α-, β- and γ-cyclodextrin, respectively, and they are obtained starting from the natural cyclodextrins by transforming them to per(6-deoxy-6-bromo)-derivatives according to a method known in the literature and subsequently subjecting the latter to the method described below as the "first method" using propylenediamine.

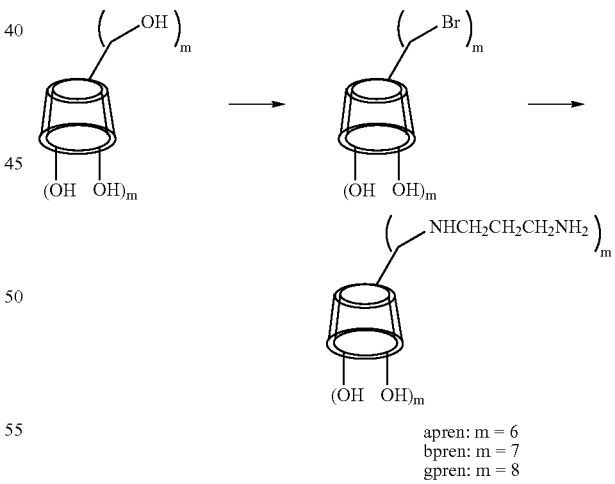

apren: m = 6
bpren: m = 7
gpren: m = 8

The invention also relates to the new molecules aguan, bguan and gguan, which bear six or seven or eight guanidino-groups in their primary side and they are prepared from the natural α-, β- and γ-cyclodextrins, respectively, converting them according to published methods sequentially to per(6-deoxy-6-bromo)-, per(6-deoxy-6-azido)-, and per(6-deoxy-6-amino)-cyclodextrins [6] and finally subjecting the latter to the method described below as the "second method":

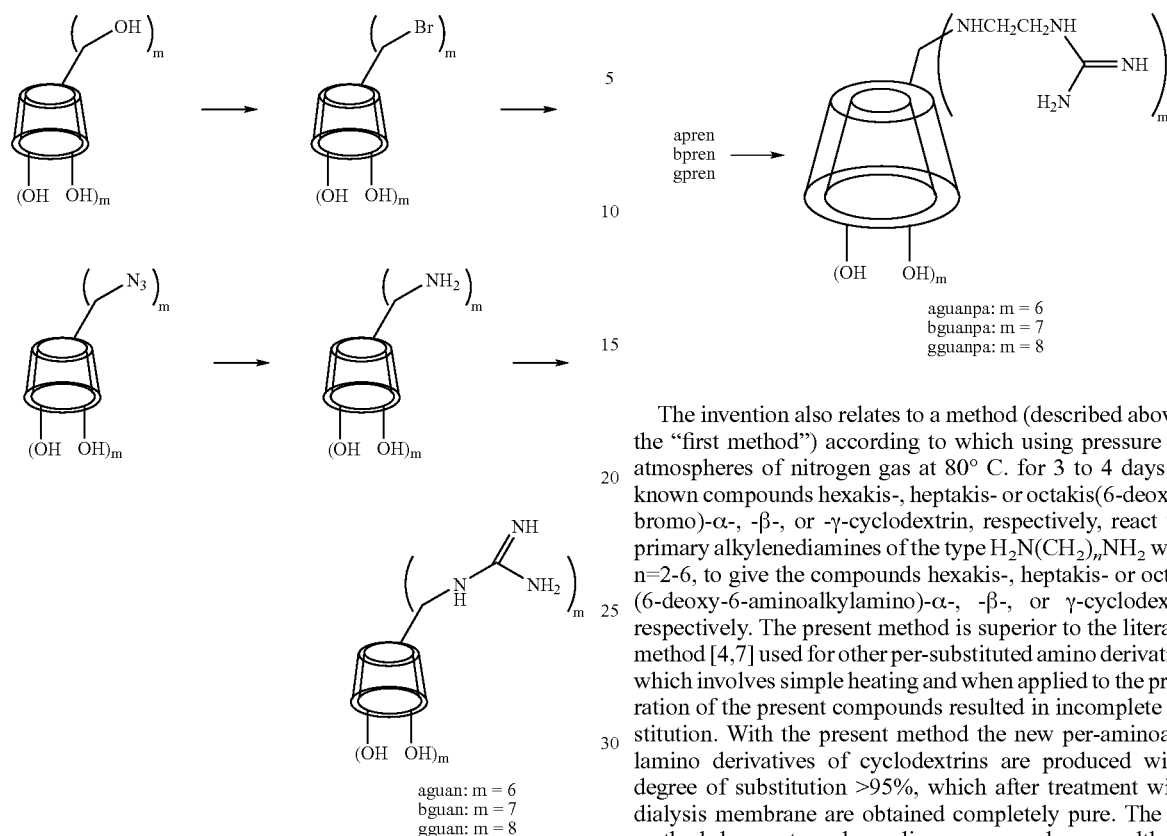

aguan: m = 6
bguan: m = 7
gguan: m = 8

The invention also relates to the new molecules aguanea, bguanea and gguanea bearing six, seven or eight guanidinoethylamino groups on their primary side, which are prepared from the new molecules apen, bpen and gpen, respectively, according to the method described below as the "second method":

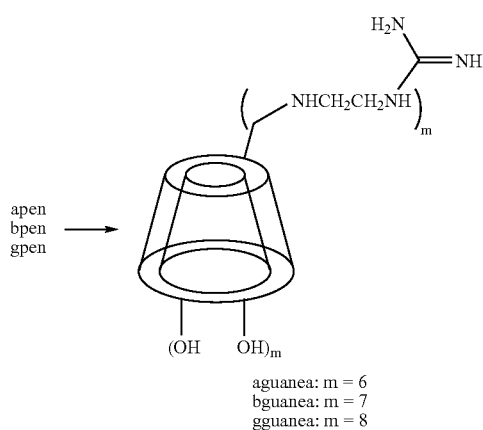

aguanea: m = 6
bguanea: m = 7
gguanea: m = 8

The invention also relates to the new molecules aguanpa, bguanpa and gguanpa bearing six or seven or eight guanidinopropylamino-groups on their primary side, which are prepared from the new molecules apren, bpren and gpren, respectively, according to the method described below as the "second method".

aguanpa: m = 6
bguanpa: m = 7
gguanpa: m = 8

The invention also relates to a method (described above as the "first method") according to which using pressure of 7 atmospheres of nitrogen gas at 80° C. for 3 to 4 days, the known compounds hexakis-, heptakis- or octakis(6-deoxy-6-bromo)-α-, -β-, or -γ-cyclodextrin, respectively, react with primary alkylenediamines of the type $H_2N(CH_2)_nNH_2$ where n=2-6, to give the compounds hexakis-, heptakis- or octakis (6-deoxy-6-aminoalkylamino)-α-, -β-, or γ-cyclodextrin, respectively. The present method is superior to the literature method [4,7] used for other per-substituted amino derivatives, which involves simple heating and when applied to the preparation of the present compounds resulted in incomplete substitution. With the present method the new per-aminoalkylamino derivatives of cyclodextrins are produced with a degree of substitution >95%, which after treatment with a dialysis membrane are obtained completely pure. The new method does not produce oligomers or polymers, although the starting materials used could result in such products of high molecular weight.

The invention also relates to the method described above as the "second method", according to which addition of several small portions of 1H-pyrazolocarboxamidine hydrochloride (pyrguan) to the known compounds in dimethylformamide (DMF) solution per(6-deoxy-6-amino)-α-, -β- and -γ-cyclodextrins or the new compounds per[6-deoxy-6-NH—$(CH_2)_n$—$NH_2$]-α-, -β- and -γ-cyclodextrins, where n=2-6, prepared via the above "first method", affords per(6-deoxy-6-guanidino)- or per(6-deoxy-6-guanidinoalkylamino)-α-, -β- and -γ-cyclodextrin, respectively, having a degree of substitution >95%, which after treatment with a dialysis membrane are obtained completely pure. The method differs from the one referring to the preparation of mono(6-deoxy-6-guanidinoalkylamino)-β-cyclodextrin [5] in that the starting cyclodextrin derivative is different, the addition of pyrguan must be done in small portions and the reaction time be at least 24 h. With the present method the produced per-substituted cyclodextrins are of high purity after dialysis, therefore laborious chromatographic purifications are not required.

The invention also relates to the use of the new compounds described above for the compaction of DNA. Specifically, the new cyclodextrin derivatives described above interact with DNA and bring about neutralization of its negative charge, therefore inducing compression of its double stranded structure. As a result, during electrophoresis in agarose gel with ethidium bromide as stain, DNA does not advance, in contrast to natural DNA, which advances along the electrophoresis path to produce a "smear". This last experiment is considered fundamental for certification of DNA compaction. The same conclusions were drawn from Atomic Force Microscopy (AFM) experiments and UV spectra. The features of the present new cyclodextrin derivatives for DNA compaction are superior to those of the recently published aminocyclodextrins [7] in that only very small concentrations of the derivatives induce effective DNA compaction. Specifically, the derivatives of the present invention described above inhibit completely the development DNA during electrophoresis at a mass/charge cyclodextrin derivative/DNA ratio which is smaller than 0.5, whereas for the literature compounds [7] the corresponding mass/charge ratio ranges between 2000 to 250, in the best cases.

The invention also relates to the use of the new compounds per(6-deoxy-6-aminoalkylamino) and per(6-deoxy-6-guanidino)- and per(6-deoxy-6-guanidino-alkylamino)-derivatives of α-, β- and γ-cyclodextrins, where alkyl=—$CH_2)_n$—, n=2-6, for transportation of molecules inside cells. The new compounds effectively pass through the membrane of cells and disperse inside the cytoplasm. This was documented by incubating the compounds suitably labeled with fluorescent tags in cell cultures. The permeation of the cell membrane was visualized by fluorescence microscopy. The quantity of the guanidine-substituted derivatives inside the cytoplasm is higher than the amino substituted ones, for the same concentration and the same incubation time; therefore we conclude that they are more effective in permeating the cell membranes. Further, the compounds are able to target DNA as shown by the observation of fluorescence localized in nucleoli (green fluorescent circles inside the cell nucleus). The above property makes the new compounds possible candidates for cellular delivery of problematic therapeutic cargos inside mammalian cells. In this respect they can act as the CCP (Cell Penetrating Peptides) analogues.

The invention also relates to pharmaceutical products that contain the above described new cyclodextrin derivatives.

The following examples are given in order to further explain the present invention and they are indicative of the methods used and the new compounds prepared:

EXAMPLE 1

Heptakis(6-deoxy-6-aminoethylamino)-β-cyclodextrin (bpen): Heptakis(6-deoxy-6-bromo)-βCD (320 mgr, 0.4 mmol) was added to ethylenediamine (3.75 ml, 56 mmol) and the mixture was agitated inside an autoclave at 80° C. under a nitrogen ($N_2$) atmosphere at pressure 7 Atm for 3-4 days. Then, the excess ethylenediamine was removed under reduced pressure and the oily residue was dissolved in methanol (5 ml). This solution was added dropwise to cold acetone (200 ml). The white precipitate formed was collected by filtration under a nitrogen atmosphere and washed with acetone (50 ml). After drying over $P_2O_5$, the solid was dissolved in doubly distilled water (3 ml), the pH of the solution was brought to 7 by addition of HCl 1N, and the solution was dialysed (Sigma dialysis cellulose tubing, benzoylated) for 3 days to remove low molecular weight substances. At the end of this period the sample was lyophilized and a pale yellow solid was collected (125 mg, yield 18%). $^1$H NMR (500 MHz, $D_2O$, 25° C.): δ (ppm) 5.06 (br, 7H, H1), 3.90 (br, 14H, H3, H5), 3.57 (br, 14H, H2, H4), 3.03 (br, 14H, H6,6'), 2.89-2.83 (br, 28H, —$CH_2CH_2NH_2$) ppm. $^{13}$C NMR (125 MHz, $D_2O$, 25° C.): δ (ppm) 104.2 (C1), 84.8 (C4), 75.6 (C5), 74.7 (C2), 73.3 (C3), 51.3 (C6,6'), 50.3 (—$NHCH_2$—), 4.16 (—$CH_2NH_2$). Elemental Analysis for $C_{56}H_{112}N_{14}O_{28}$·8HCl·5$H_2O$: Calcd. C 37.13; H 7.23; N, 10.83. Found: C 37.14; H 7.34; N 9.98.

In order to calculate with accuracy the mass/charge ratio for DNA interactions (see example 7 below), the solution (before dialysis) was allowed to stir in the presence of an anion exchange resin (Cl$^-$ anions, Dowex Type I 1×2-400) for 1 h and then the resin was filtered off. Spectrophotometric analysis showed that the compound contains 8 equivalents of Cl$^-$, therefore is octakis protonated.

EXAMPLE 2

Heptakis(6-deoxy-aminopropylamino)-β-cyclodextrin (bpren): The synthesis of bpren was carried out starting from heptakis(6-deoxy-6-bromo)-βCD following the procedure described previously for bpen. The product was collected as a yellow solid (207 mg; yield 38%). $^1$H NMR (500 MHz, $D_2O$, 25° C.): δ (ppm) 5.07 (br, 7H, H1), 3.89 (br, 14H, H3, H5), 3.58 (br, 7H, H2), 3.51 (br, 7H, H4), 3.00 (br, 14H, —$NHCH_2$—), 2.92 (br, 14H, H6,6'), 2.72 (br, 14H, —$CH_2NH_2$), 1.84 (br, 14H, —$CH_2$—) ppm. $^{13}$C NMR (125 MHz, $D_2O$, 25° C.): δ (ppm) 104.5-103.7 (C1, br), 86.9-84.4 (C4, br), 75.4 (C3), 74.7 (C2), 72.8 (C5), 51.7 (—$NHCH_2$—), 49.5 (C6), 40.7 (—$CH_2NH_2$), 29.2 (—$CH_2$—). Elemental Analysis for $C_{63}H_{126}N_{14}O_{28}$·10HCl·3$H_2O$: Calcd. C 38.88; H 7.35; N 10.07. Found: C 38.90; H 7.70; N 8.85.

EXAMPLE 3

Octakis(6-deoxy-6 aminoethylamino)-γ-cyclodextrin (gpen): The synthesis of gpen was carried out starting from octakis(6-deoxy-6-bromo)-γCD according to the procedure described previously for bpen. The product was collected as a pale yellow solid (71 mg, yield 18% calculated for 10HCl salt). $^1$H NMR (500 MHz, $D_2O$, 25° C.): δ (ppm) 5.12 (br, 8H, H1), 3.88 (br, 16H, H3, H5), 3.58 (br, 16H, H2, H4), 3.02 (br, 16H, —$CH_2NH_2$), 2.88 (br, 32H, —$NHCH_2$—, H6,6'). $^{13}$C NMR (125 MHz, $D_2O$, 25° C.): δ (ppm) 103.9-103.3 (C1, br), 83.8-83.2 (C4, br), 75.3 (C3), 74.9 (C2), 73.2 (C5), 51.3 (C6), 49.2 (—$NHCH_2$—), 41.4 (—$CH_2NH_2$). Elemental Analysis for $C_{64}H_{128}N_{16}O_{32}$·7HCl·4$H_2O$: Calcd. C 39.20; H 7.35; N 11.43. Found: C 39.17; H 7.38; N 10.03.

EXAMPLE 4

Heptakis(6-deoxy-6-guanidino)-β-cyclodextrin (bguan): Heptakis(6-deoxy-6-amino)-β-cyclodextrin (667 mg, 0.59 mmol) was dispersed in dry dimethylformamide (DMF, 6.5 ml) and in the mixture 1H-pyrazole-1-carboxamidine hydrochloride (28 eq, 16.55 mmol, 2.4 g) and N,N'-diisopropylethylamine (28 eq, 16.35 mmol, 2.29 ml) were added. The whole was allowed to stir at 70° C. for 21 h under a nitrogen atmosphere and a sticky solid was formed. Then, diethyl ether was added dropwise (200 ml) and the suspension formed was stirred for 2 h. The ether was decanted and the collected sticky solid was dissolved in a very small amount of water (6 ml). Addition of ethanol resulted in the precipitation of a white substance, which was filtered and air-dried. A white solid was recovered which after purification in a dialysis membrane (Sigma benzoylated tubing) for 48 h and lyophilization was pure (213 mg, yield 32%), and its solubility in water was 59 mM. Spectrophotometric analysis showed that the compound is holding 8 equivalents of Cl$^-$ anions, so it is octakis protonated: $^1$H NMR (500 MHz, DMSO, 300 K): δ (ppm) 7.87 (br, s, 7H, —C═NH), 7.24 (br, s, 14H, —$NH_2$), 5.97 (br, s, 7H, —OH2), 5.85 (br, s, 7H, OH3), 4.96 (7H, H1), 3.83 (br, m, 7H, H5), 3.64 (br, m, 7H, H3), 3.53 (m, 7H, H6), 3.40 (br, m, 21H, H6', H2, H4). $^1$H NMR (500 MHz, $D_2O$, 300 K): δ (ppm) 5.20 (d, J=3.3 Hz, 7H, H1), 4.00 (t, J=9.7 Hz, 7H, H5), 3.92 (t, J=9.5 Hz, 7H, H3), 3.65 (dd, J=3.5 Hz, J=9.5 Hz, 7H, H2), 3.61 (d, J=14.9 Hz, 7H, H6), 3.43 (m, 14H, H4, H6'). $^{13}$C NMR (125 MHz, $D_2O$, 300K): δ (ppm) 158.2 (—C═), 102.2

(C1), 82.9 (C4), 72.8 (C5), 72.1 (C2), 71.2 (C3), 42.6 (C6). $^{15}$N NMR (50.66 MHz, D$_2$O, 300 K, conc. 1.5 M, D1=60 s): δ (ppm) 78.5 (=NH), 72.3 (—NH$_2$). MS (ESI, positive ion mode), calculated: M+=1422.4, found: m/q: 204.3 (M+/7q, 100%), 1423 (MH$^+$, 5%). Exact mass for [C$_{49}$H$_{91}$O$_{28}$N$_{21}$.HCl.Na]+: Calcd: 1480.6006. Found: 1480.7453. Elemental analysis for [C$_{49}$H$_{91}$O$_{28}$N$_{21}$.13HCl.H$_2$O]: calcd: C 30.74; H 5.58; N 15.36. Found: C 31.00; H 5.80; N 15.40.

EXAMPLE 5

Octakis(6-deoxy-6-guanidino)-γ-cyclodextrin (gguan): Octakis(6-deoxy-6-amino)-γ-cyclodextrin (560.9 mg, 0.435 mmol) was dispersed in dry dimethylformamide (DMF, 5.6 ml) and in the mixture 1H-pyrazole-1-carboxamidine hydrochloride (37 eq, 16 mmol, 2.35 g) και N,N'-diisopropylamine (25 eq, 5 mmol, 1.9 ml) were added in three equal portions during 3 days. The mixture was allowed to stir for 72 h at 70° C. under a nitrogen atmosphere. Then diethyl ether (180 ml) was added dropwise and the resulting suspension was stirred for 2 h. The ether was removed under reduced pressure and the relatively sticky solid was dissolved in a very small amount of water. Addition of ethanol afforded a white solid (454 mg after drying) which was dialysed (Sigma benzoylated tubing) for 48 h and lyophilized. A pure white substance was collected (197.4 mg, 24%). Spectrophotometric analysis showed that 10 equivalents of Cl$^-$ anions are held in the molecule, it is, therefore, decakis protonated. $^1$H NMR (500 MHz, D$_2$O, 300 K): δ (ppm) 5.14 (slightly br, 8H, H1), 4.05 (m, 8H, H5), 3.90 (t, J=9.3 Hz, 8H, H3), 3.63 (dd, J=3.6 Hz, J=9.8 Hz, 8H, H2), 3.58 (d, J=14.5 Hz, 8H, H6), 3.54-3.45 (m, 16H, H4, H6'). $^{13}$C NMR (125 MHz, D$_2$O, 300 K): δ (ppm) 158.0 (—C=NH), 101.0 (C1), 81.0 (C4), 73.0 (C5), 72.9 (C2), 72.8 (C3), 41.0 (C6). Exact mass calculated for [C$_{56}$H$_{104}$O$_{32}$N$_{24}$.4HCl.Na]$^+$=1791.6213. Found: 1791.6920. MS (ESI, positive ion mode) m/q: 162 (methyl guanidine hydrate fragment, 100%).

EXAMPLE 6

Heptakis(6-deoxy-6-guanidinoethylamino)-β-cyclodextrin (bguanea): Heptakis(6-deoxy-6-aminoethylamino)-βCD (bpen) (208 mg, 0.12 mmol) was dissolved in dry DMF (10 ml) and then a mixture of 1H-pyrazole-1-carboxamidine hydrochloride (1.23 gr, 8.4 mmol) and N,N'-diisopropylamine (1.65 ml, 9.7 mmol) was added in three equal portions during 3 days. The reaction mixture was stirred at 70° C. under a N$_2$ atmosphere. The solution was then cooled to room temperature and diethyl ether was added dropwise (150 ml), resulting in the formation of a sticky solid. After agitation for 2 h the solvent was decanted and the solid was dissolved in H$_2$O (2 ml). To this solution ethanol was added (200 ml) and the precipitate that resulted was washed with ethanol (50 ml). After air-drying the solid underwent anion exchange, dialysis and lyophilization, following the method described above for bpen. Finally, the product (70 mg, 29%) was collected as a pale yellow solid. Spectrophotometric analysis revealed 8 equivalents of Cl$^-$ anions associated with the molecule, that is, the product is octakis protonated. $^1$H NMR (500 MHz, D$_2$O, 25° C.): δ (ppm) 5.04 (br, 7H, H1), 3.89 (br, 14H, H3, H5), 3.57 (br, 14H, H2, H4), 3.25 (br, 14H, —CH$_2$NH$_2$), 2.79 (br, 28H, —NHCH$_2$—, H6,6'). $^{13}$C NMR (125 MHz, D$_2$O, 25° C.): δ (ppm) 159.9 (—C=), 104.3 (C1), 85.0 (C4), 75.5 (C5), 74.7 (C2), 73.3 (C3), 51.5 (C6), 50.7 (—NHCH$_2$—), 43.6 (—CH$_2$NH$_2$). Elemental Analysis for C$_{63}$H$_{126}$N$_{28}$O$_{28}$.8HCl.5H$_2$O: calcd. C 35.94; H 6.89; N 18.63. Found. C 36.06; H 6.68; N 17.48.

All new substances included in the invention were used for DNA compaction. One such use is described in example 7 below.

EXAMPLE 7

DNA Compaction

Double stranded DNA is negatively charged, therefore if placed inside an agarose gel and is subjected to a voltage differential during an electrophoresis experiment it moves towards the positive pole. Ethidium bromide is a substance that intercalates into the nucleic bases of DNA and fluoresces under UV light. When a DNA solution is placed together with ethidium bromide into a small cut (well) of the gel and is subjected to electrophoresis, its motion can be visualized under UV light since the ethidium bromide moves with it and lightens up its path. DNA is characterized by a wide distribution of molecular weights, therefore it displays a continuous fluorescent band along the entire path (smear). The overall structure of double stranded DNA changes when an adequate portion of its negative charge is neutralized, thus inducing coiling of the strands and compaction of the macromolecule. In this case, under electrophoresis conditions compact DNA does not advance at all, but stays in the well unaffected by the voltage differential. The interaction of one of the new compounds, bguan, with ultrapure calf thymus DNA 13 kb (7.6× 10$^{-4}$ M) was studied using electrophoresis in agarose gel, with ethidium bromide as the stain as shown in Table 1 (A to H and a to f are different wells of the gel). As control substances (blind experiments) guanidine hydrochloride solution (1.1.6×10$^{-4}$ M) and β-cyclodextrin solution (0.882×10$^{-4}$ M) were used. The concentrations of bguan used (1.01×10$^{-4}$ M) were calculated so that the ratio mass/charge is equal to the ratio mass/charge of DNA. The volumes shown in Table 1 were used (1λ=1 μl). In wells B, F and c, which contain 10λ of a given substance, the ratio mass/charge of the compound used to that of the DNA is ~1:1.

The experiment was carried out as follows: The same amount of DNA solution (1λ) is placed inside each well with the amounts of the substances shown in Table 1 and electrophoresed. Wells A and a are loaded with the DNA marker λHinIII of known molecular weight distribution. Wells B-C-D-E-F-G-H-b are blind experiments and contain control substances, i.e. guanidine hydrochloride (B, C, D, E) and natural cyclodextrins (F, G, H, b). Wells c-d-e-f contain the new substance bguan in varying amounts. Ethidium bromide was added in every well.

TABLE 1

| Volumes of substances during DNA electrophoresis | |
|---|---|
| A: marker DNA λHinIII | a: marker DNA λHinIII |
| B: guanidine.HCL 10 λ | b: β-cyclodextrin 1 λ (diluted 1:10) |
| C: guanidine.HCL 5 λ | c: bguan 10 λ |
| D: guanidine.HCL 1 λ | d: bguan 5 λ |
| E: guanidine.HCL 1 λ (diluted 1:10) | e: bguan 1 λ |
| F: β-cyclodextrin 10 λ | f: bguan 1 λ (stock solution diluted 1:10) |
| G: β-cyclodextrin 5 λ | |
| H: β-cyclodextrin 1 λ | |

It is observed that the control substance, β-cyclodextrin, as well as positively charged guanidine hydrochloride, under the electrophoresis conditions do not display any kind of interaction with DNA, which is normally electrophoresed.

On the contrary, the mobility of DNA is completely stalled in the wells c and d and partial inhibition is observed in the wells with smaller amounts of bguan, e and f (see Table 1), therefore it is concluded that bguan compacts DNA at a mass/charge ratio of ~0.45 or less.

The DNA-bguan interaction was confirmed with UV absorption spectra. The absorption maximum and the shape of the absorbance curve of DNA changed appreciably in the presence of 1 equivalent bguan, indicating a distinct change of its structure in buffer solution. In addition, when a 5 kbp DNA was examined under the atomic force microscope (AFM) in the tapping mode, nematoid (long warm-like) formations of up to 1 µm were observed. When this DNA was incubated with bpen complete absence of the elongated forms was observed and round nanoparticles of diameter of about ~40 nm were observed. This actually proves that DNA compacts not in big aggregates but in nanoparticles of size suitable to cross a cell membrane.

EXAMPLE 8

Cell Penetration

The ability of the new compounds, bpen, bguanea and gpen, to enter HeLa cells (human malignant cell line derived from cervical carcinoma) was studied in vitro by fluorescence microscopy. For this purpose, the above compounds were labeled with fluorescein isothiocyanate (FITC) at an approximate degree of 5% resulting in bpenFITC, bguaneaFITC and gpenFITC, respectively. As control substances (blind experiments) for the fluorescence microscopy experiments a βCD/fluorescein (200 µM/10 µM) solution and a FITC solution (20 µM) were used. In the case of the second control, the FITC used had been previously subjected to the same procedure as the one used for the labeling of bpen, bguanea and gpen, without the presence of the latter compounds. Cells were cultured in DMEM (low glucose, 1 g/L) supplemented according to ATCC protocols with 10% FBS and antibiotics, plated in six-well plates and incubated at 37° C. and 5% humidified $CO_2$ for 24 h. Immediately before incubation with the new compounds, the growth medium was replaced with fresh one and incubation at 37° C. and 5% humidified $CO_2$ continued for 10 more min. Subsequently, various volumes of 1 mM bpenFITC, bguaneaFITC or gpenFITC solutions were added to each well, so as to reach 100 or 200 µM concentrations of each compound inside the wells. After incubation at 37° C. and 5% humidified $CO_2$ for 1 h, the medium was removed and the cells were washed with fresh medium (3×1 ml), fixed with cold ethanol and left for 10 min at −15° C. before microscopic examination. Fluorescence microscopy revealed that cells incubated with the control substances, βCD/fluorescein and treated FITC, did not show any fluorescence inside their cytoplasm. In contrast, cells that were treated with bpenFITC, bguaneaFITC and gpenFITC showed intense fluorescence inside the cytoplasm in the form of localized spots. The fluorescence of cells treated with bguaneaFITC was much more intense than the corresponding treated with bpenFITC and gpenFITC. An intriguing observation was the appearance of the nucleoli as green-fluorescent circular formations.

REFERENCES

[1] (a) Szejtli, J. *Cyclodextrin Technology* Kluwer Academic Publishers, Dordrecht, 1988; (b) Szejtli, J. *Chem. Rev.* 1998, 98, 1743. (c) Hedges, A. R. *Chem. Rev.* 1998, 98, 2035.

[2] (a) French Anderson, W. *Nature,* 1998, 392, 25. (b) Friedman, Scientific American 1997, 276, 80.

[3] (a) Gershon, H.; Ghirlando, R.; Guttman, S. B.; Minsky, A. *Biochem.* 1993, 32, 7143. (b) Huang, L.; Lee, R. J. *J. Biol. Chem.* 1996, 271, 8481. (c) Garrett, S. W.; Davies, O. R.; Milroy, D. A.; Wood, R. J.; Pouton, C. W.; Threadgill, M. D. *Bioorg. Med. Chem.* 2000, 8, 1779. (d) Dubruel, P.; Christiaens, B.; Vanloo, B.; Bracke, K.; Rosseneau, M.; Vandekerckhove, J.; Schacht, E. *Eur. J. Pharm. Sci.* 2003, 18, 211.

[4] D. Vizitiu, C. S. Walkinshaw, B. I. Gorin, G. R. J. Thatcher, *J. Org. Chem.,* 1997, 62, 8766.

[5] Smith, P. J.; Cotner, E. S. *J. Org. Chem.* 1998, 63, 1737.

[6] (a) Hwang S. J.; Bellocq, N.; Davis, M. E. *Bioconjugate Chem.* 2001, 12, 280. (b) Pun, S. H.; Davies, M. E. *Bioconjugate Chem.* 2002, 13, 630. (c) Davies, M. E.; Bellocq, N. *J. Incl. Phenom. Macrocyclic. Chem.* 2002, 44, 17. (d) Popielarski, S. R.; Mishra, S.; Davis, M. E. *Bioconjugate Chem.* 2003, 14, 672.

[7] Cryan, S.-A.; Holohan, A.; Donohue, R.; Darcy, R.; O'Driscoll, C. M. *Eur. J. Pharm. Sci.* 2004, 625.

The invention claimed is:

1. Compounds of type per(6-deoxy-6-substituted)-cyclodextrins consisting of:
   hexakis(6-deoxy-6-NH(CH$_2$)$_n$—R$^1$)-α-cyclodextrin, wherein
   (a) R$^1$ equals NH$_2$ (amino group) and n equals 3 or 4 or 5 or 6; or
   (b) R$^1$ equals C(=NH)NH$_2$ and n equals zero; or
   (c) R$^1$ equals NHC(=NH)NH$_2$ (guanidino group) and n equals 2 or 3 or 4 or 5 or 6; and
   heptakis(6-deoxy-6-NH(CH$_2$)$_n$—R$^1$)-β-cyclodextrin, wherein
   (d) R$^1$ equals NH$_2$ (amino group) and n equals 3 or 4 or 5 or 6; or
   (e) R$^1$ equals C(=NH)NH$_2$ and n equals zero; or
   (f) R$^1$ equals NHC(=NH)NH$_2$ (guanidino group) and n equals 2 or 3 or 4 or 5 or 6; and
   octakis(6-deoxy-6-NH(CH$_2$)$_n$—R$^1$)-γ-cyclodextrin, wherein
   (g) R$^1$ equals NH$_2$ (amino group) and n equals 2 or 3 or 4 or 5 or 6; or
   (h) R$^1$ equals C(=NH) NH$_2$ and n equals zero; or
   (i) R$^1$ equals NHC(=NH)NH$_2$ (guanidino group) and n equals 2 or 3 or 4 or 5 or 6.

2. The compound heptakis(6-deoxy-6-aminoethylamino)-β-cyclodextrin (bpen).

3. The compounds according to claim 1, where n equals zero and R$^1$ equals C(=NH)NH$_2$, which are hexakis(6-deoxy-6-guanidino)-α-cyclodextrin (aguan) and heptakis(6-deoxy-6-guanidino)-β-cyclodextrin (bguan) and octakis(6-deoxy-6-guanidino)-γ-cyclodextrin (gguan).

4. The compounds according to claim 1:
   wherein R$^1$ equals NH$_2$ (amino group) and n equals 2, which are octakis(6-deoxy-6-aminoethylamino)-γ-cyclodextrin (gpen); and
   wherein R$^1$ equals NH$_2$ (amino group) and n equals 3, which are hexakis(6-deoxy-6-aminopropylamino)-α-cyclodextrin (apren) and heptakis(6-deoxy-6-aminopropylamino)-β-cyclodextrin (bpren) and octakis((6-deoxy-6-aminopropylamino)-γ-cyclodextrin (gpren).

5. The compounds according to claim 1:
   wherein R$^1$ equals NH—C(=NH)NH$_2$ (guanidino group) and n equals 2, which are hexakis(6-deoxy-6-guanidinoethylamino)-α-cyclodextrin (aguanea), heptakis(6-deoxy-6-guanidinoethylamino)-β-cyclodextrin (bguanea) and octakis (6-deoxy-6-guanidinoethylamino)-γ-cyclodextrin (gguanea); and wherein $R^1$ equals NH—C(=NH)NH$_2$ (guanidino group) and n equals 3, which are hexakis (6-deoxy-6-guanidinopropylamino)-α-cyclodextrin (aguanpa), heptakis(6-deoxy-6-guanidinopropylamino)-β-cyclodextrin (bguanpa) and octakis(6-deoxy-6-guanidinopropylamino)-γ-cyclodextrin (gguanpa).

6. Pharmaceutical product that contains compounds according to claim 1.

7. A method for DNA compaction comprising contacting DNA with one or more of the compounds according to claim 1.

8. A method for cell permeation and intracellular delivery comprising contacting the cell with one or more of the compounds according to claim 1, and in the case of intracellular delivery, wherein the one or more compounds is in contact with a substance or substances being delivered to the cell.

* * * * *

UNITED STATES PATENT AND TRADEMARK OFFICE
CERTIFICATE OF CORRECTION

PATENT NO. : 7,834,174 B2
APPLICATION NO. : 11/662450
DATED : November 16, 2010
INVENTOR(S) : Mavridis et al.

It is certified that error appears in the above-identified patent and that said Letters Patent is hereby corrected as shown below:

Title page, Item (54) and at Column 1, lines 1-5, Title, should read

--PER-6-GUANIDINO-, ALKYLAMINO-CYCLODEXTRINS, METHODS OF THEIR SYNTHESIS AND THEIR USE FOR THE COMPACTION OF DNA AND INTRACELLULAR DELIVERY--

Title page, Item (76) Inventors should read

--Irene M. Mavridis, 15 Panagiotou St., Papagou, GR-156 69 Athens (GR); Konstantina Yannakopoulou, 49 28th Octovriou St., Vrilissia, GR-152 35 Athens (GR); Kyriaki Eliadou, 10 Costi Palama, Kaisariani, GR-161 22 Athens (GR); Nikolaos Mourtzis, 21 Nikomideas, Peristeri, GR-121 34 Athens (GR); Chrysi Aggelidou, 18 Vera & Andromachis, Palaio Faliro, GR-175 64 Athens (GR)--

Signed and Sealed this
Fifteenth Day of February, 2011

David J. Kappos
*Director of the United States Patent and Trademark Office*